United States Patent [19]

Stevenson

[11] Patent Number: 5,101,770

[45] Date of Patent: Apr. 7, 1992

[54] POST-MILKING AND PRE-MILKING UDDER CARE

[76] Inventor: Dale V. Stevenson, 940 Lake Shore Way B-23, Lake Alfred, Fla. 33850

[21] Appl. No.: 608,918

[22] Filed: Nov. 5, 1990

[51] Int. Cl.⁵ .............................................. A01K 29/00
[52] U.S. Cl. ................................................. 119/159
[58] Field of Search ...................... 119/14.01, 158, 159

[56] References Cited

U.S. PATENT DOCUMENTS

| | | | |
|---|---|---|---|
| 3,554,166 | 1/1971 | Belden | 119/159 |
| 3,950,554 | 4/1976 | Prince | 514/873 X |
| 4,025,628 | 5/1977 | Dewey et al. | 514/241 X |
| 4,067,967 | 1/1978 | Prince | 514/404 X |
| 4,070,469 | 1/1978 | Haber et al. | 514/312 |
| 4,113,854 | 9/1978 | Andrews et al. | 524/53 X |
| 4,199,602 | 4/1980 | Lentsch | 514/727 |
| 4,258,056 | 3/1981 | Lentsch | 514/566 |
| 4,347,312 | 8/1982 | Brown et al. | 435/188 X |
| 4,376,787 | 3/1983 | Lentsch et al. | 514/576 |
| 4,610,993 | 9/1986 | Wedig et al. | 514/335 |
| 4,935,248 | 6/1990 | Witkin | 424/671 X |

*Primary Examiner*—Gene Mancene
*Assistant Examiner*—Thomas Price
*Attorney, Agent, or Firm*—Charles A. McClure

[57] ABSTRACT

Post-milking and pre-milking udder care to assure udder disinfection, including coloring the udder after milking and decolorizing the udder before milking. The post-milking step includes applying thereto an aqueous solution of an alkali metal hypochlorite and an alkali metal permanganate, whereas the pre-milking step includes applying thereto an aqueous solution of a peroxide and an organic acid. Preferred component compositions include sodium hypochlorite, potassium permanganate, hydrogen peroxide, and acetic acid.

12 Claims, 1 Drawing Sheet

POST-MILKING AND PRE-MILKING UDDER CARE

TECHNICAL FIELD

This invention relates to udder care of domestic animals milked for human benefit, especially compositions and methods of disinfecting the udder, including the teats, to safeguard against infection.

BACKGROUND OF THE INVENTION

Sanitation in food preparation is usually principally for the direct benefit of the consumer, but where the food is produced by a living animal, as in the instance of milk, it is also desirable to safeguard the health of the animal—as well as the product output rate or quantity and its condition—by taking suitable sanitary precautions. The udder and particularly the teats of milk animals are highly susceptible to infection from contact with flies, manure, people's hands, etc., so good milking technique includes application of suitable disinfecting compositions.

For many years the preferred germicide in disinfectants for such use has been iodine, which in elemental form is not soluble in water (though some of its salts and other combined forms are) but is soluble in alcohol and many other organic liquids. Its traditional popularity stems in part from the characteristically intransigent stain it leaves as visible evidence of its application. However, it and its customary liquid formulations foster chapping and cracking, which not only are painful but also provide new sites for infection.

Iodophoric compositions advanced as less troublesome are found in these representative U.S. Pat. Nos. Hall 3,663,694 (ethoxylated lanolin), Eckols 4,012,504 (mineral oil, with polyoxyethylene cetyl ether), Foll et al. 4,288,428 (alkylphenoxypoly[ethyleneoxy]ethanol or polyvinylpyrrolidone), and Lauermann et al. 4,466,959 (glycerin, paraffin oil, and higher fatty acids). Such efforts suggest that there is a need for further improvements in this art, preferably a new departure rather than simply more—or more varied—iodophors.

Other germicides have been made the basis of disinfectants for udder treatment. The efficacy of chlorine-containing compositions, specifically hypochlorites ("Clorox") is reported in *Journal of Diary Science*, vol. 56, no. 1, p. 148 (January 1973) and references cited therein. However, they have not been generally accepted, regardless of efficacy—in part because of tradition, and in part because of lack of coloring or equivalent identifiability so as to assure positive monitoring that the treatment has been accomplished.

Lasting colorizers of hypochlorite bleaches used for different purposes also are identified in such U.S. Pat. Nos. as Kitchen et al. 3,544,373 (phthalocyanines), Hung 4,536,367 (triphenylmethanes), and Sudbury 4,457,855 (anthraquinones), for example. However, they are not suitable for the present purpose because of their persistence.

Prince U.S. Pat. No. 3,950,554, while urging the use of a fatty acid ester plus drying oil to form a water-resistant film on udders, included a suggestion of an edible organic dye, such as carotene, as well as hypochlorites, iodophors, and/or other udder disinfectants. His teachings failed to make any appreciable impression on the art, at least in the direction suggested above as desirable.

SUMMARY OF THE INVENTION

A primary object of the present invention is to ascertain that udders of milking animals are subjected to timely disinfection.

Another object of this invention is to ameliorate the undesired side-effects characteristic of iodophoric disinfection of udders.

A further object is to attain the foregoing and related objects efficiently and economically.

In general, the objects of the present invention are attained, in a method of post-milking and pre-milking udder care, by coloring such udder in a post-milking disinfecting step, and decolorizing and preferably also disinfecting it at the next pre-milking treatment, without resorting to iodine, non-aqueous liquids, organic dyes, etc.

More particularly, according to this invention, at post-milking a coloring and disinfecting step is performed using a hypochlorite colored with a permanganate. At pre-milking a decolorizing and disinfecting step is performed with a peroxide and an organic acid.

Other objects of the present invention, together with means and methods for attaining the various objects, will be apparent from the following description and accompanying diagrams of preferred embodiments, which are presented by way of example rather than limitation.

DESCRIPTION OF THE INVENTION

Figure 1:
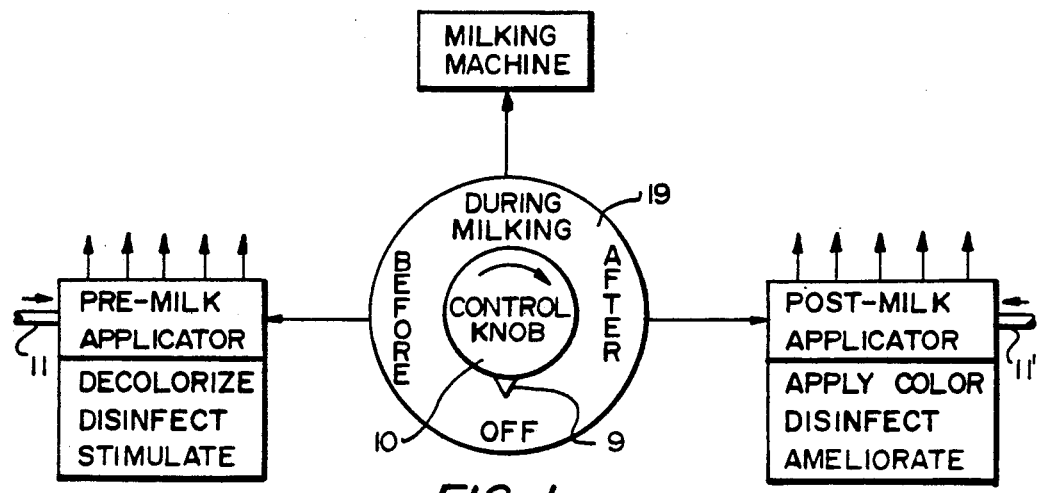
FIG. 1 is a schematic diagram of apparatus useful in practicing this invention.

FIG. 1 shows schematically control knob 10 (curved arrow shows setting order) plus pointer 9 and scale 19, with four positions at main compass points marked BEFORE (west), DURING (north), and AFTER (east) MILKING, and OFF (south). A north arrow designates a MILKING MACHINE conveniently actuatable by the control knob. Such a machine may (and usually would) be conventional in design and operation, may be actuated separately instead of by such knob, and is not shown or described because it may even be omitted as not being a part of this invention—which is compatible with performance of milking by hand.

Arrows to the west and east scale positions designate PRE-MILK and POST-MILK applicators, respectively, either a single device used to apply respective compositions sequentially, or optionally distinct devices each dedicated to applying its particular composition. Tubes 11, 11, suggest liquid supply to the respective applicators. Short arrows pointing up from each applicator block are suggestive of their function in applying liquid upward to an overlying udder. Blocks under the respective applicator blocks list their functions: the PRE-MILK method steps, DECOLORIZE, DISINFECT, and STIMULATE; and the POST-MILK method steps, APPLY COLOR, DISINFECT, and AMELIORATE. These functions are considered further in method terms hereinafter.

Figure 2:
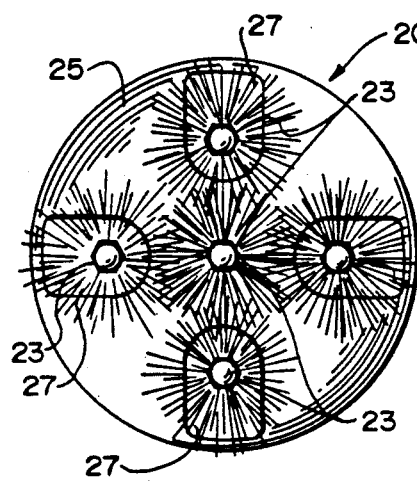
FIG. 2 is a plan view of applicator apparatus similarly useful.
Figure 3:
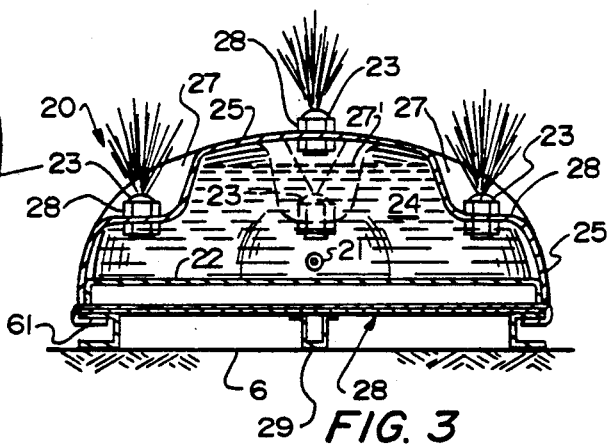
FIG. 3 is a side elevation of the apparatus of FIG. 2.

FIGS. 2 and 3 show in plan and in side elevation, respectively, applicator 20 suited to the practice of the present invention. Such 14. applicator, shown here by way of example, is further illustrated and described by Belden in U.S. Patent 3,544,166. Flat circular base plate 28 rests on feet 29 underlying it at the compass points and supports reinforcing envelope 22 over its entire upper surface. The envelope in turn is overlain by domed cover 25. Nozzle cavities 27 are recessed around five nozzles 23 directed upward from individual apertures 28 in the domed cover, within four respective nozzle cavities 27 recessed in the cover at quadrantal intervals about the center, and one at the dome center 27,. Compartment 24 formed between the cover and the envelope is shown containing the appropriate liquid received through pipe 21 from an external source (not shown).

Figure 4:
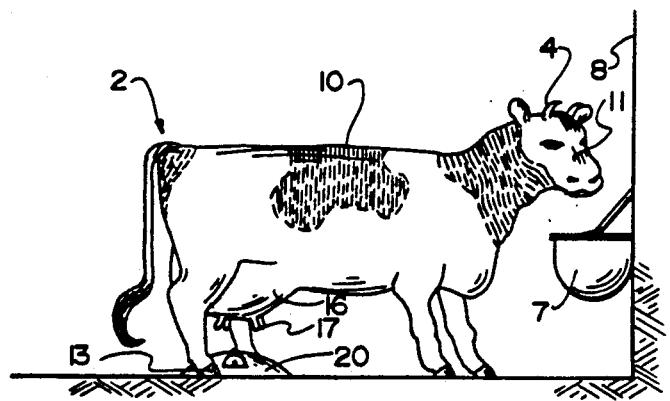
FIG. 4 is a side elevation of such apparatus, reduced in scale, and with a milk animal shown appropriately positioned above it.

FIG. 4 shows in side elevation, milk cow 30 in milking stall 32 defined by floor 31 supporting the cow and by wall 38 supporting feed container 37, which aids in orienting the cow therein so that applicator 20 underlies overhanging udder 36 with teats 34. Rear hooves 33 (one visible) of the cow flank the applicator, whose sloping domed cover is unlikely to have a hoof stand thereon even though the applicator is resting on the floor as shown. The floor is an alternative to a dolly or trolley (which may be employed instead, if preferred) and leaves plenty of space to swing the teat cups and connecting tubes of a milking machine (not shown) into an appropriate position. A second such applicator can be located near (or appended to) the one shown, for the PRE-MILK or the POST-MILK application, but is omitted here in the interest of simplicity of illustration.

Operation of the illustrated apparatus to practice the method of this invention is readily understood from the foregoing diagrams, the accompanying description, and these remarks. For simplicity it is assumed that only one applicator is used, although (as already indicated) separate ones may be dedicated to the respective treating compositions. In either event the treating compositions are pumped under sufficient force to spray upward appropriately onto the overhanging udder. Any excess liquid will drip onto the applicator and from there to the floor or to the floor directly and presumably will flow to a drain (not shown) or be absorbed by material o the floor.

The PRE-MILK and POST-MILK compositions are preferably formulated somewhat in advance of use, although in a large dairy it would be feasible to combine the respective ingredients just ahead of the applicators, if desired. Both are dilute aqueous solutions and are kinder to the udder than iodophors are, even with emollients added.

The PRE-MILK solution comprises about several percent peroxide and several percent lower aliphatic acid, preferably hydrogen peroxide and acetic acid. Such solution may be formulated by adding one part of glacial acetic acid to about thirty parts of the readily commercially available 3% aqueous hydrogen peroxide. Alternatively, a corresponding lesser amount of higher strength hydrogen peroxide solution can be diluted accordingly. Such solution has disinfecting qualities and a decolorizing capability considered further below. Spraying it vigorously onto the udder is conducive to the ensuing milking because it stimulates the animal to "let down" the milk.

The POST-MILK solution comprises several percent hypochlorite and a lesser coloring amount (at least a trace) of permanganate, both alkali metal compositions, preferably sodium hypochlorite and potassium permanganate. All erstwhile chemistry students recognize the persistent characteristic purplish brown stain of permanganate. Emollients, such as lanolin, may be added to ameliorate effects of milking and of frequent application of disinfectants upon the udder. A permanganate-stained udder shows at a glance that it was treated with disinfectant (and optionally with one or more such emollients).

At the next ensuing PRE-MILK session, application of the acidic solution of hydrogen peroxide converts the permanganate to the colorless manganate and releases oxygen gas of twice the volume available from the hydrogen peroxide, a strong disinfecting action. The clean udder is then subjected to another coloring permanganate application at the next POST-MILK session after intervening milking, and so on.

If desired, the whole procedure can be accomplished manually by dip cup and sponge, given the appropriate compositions, but a semiautomated procedure is preferable. Other apparatus may be used in like manner with appropriate adaptation to the inventive method. Spray outlets different in number and orientation from those shown may be substituted, with or without additional desirable features.

Advantages and benefits of the apparatus and the method of this invention have been mentioned and are readily recognizable. Others doubtless will accrue to persons who practice the invention--and to the animals upon which they practice it.

Preferred embodiments and variants have been suggested for this invention. Other modifications may be made, as by adding, combining, deleting, or subdividing compositions, parts, or steps, while retaining all or some of the advantages and benefits of the present invention—which itself is defined in the following claims.

The claimed invention:

1. A method of post-milking and pre-milking udder care, comprising
    coloring such udder in a post-milking disinfecting step with an iodine-free inorganic coloring composition comprising a permanganate; and
    decolorizing such udder in a pre-milking disinfecting step.

2. A method of post-milking and pre-milking udder care, comprising the steps of
    applying thereto at post-milking, a solution of colored disinfecting composition comprising a dissolved permanganate, and
    applying thereto at post-milking, a solution of colored disinfecting composition comprising a dissolved permanganate, and
    applying thereto at the next pre-milking, a decolorizing composition effective to decolorize the previously applied colored disinfecting composition.

3. Method of udder care according to claim 2, wherein such decolorizing composition also comprises an organic acid.

4. Method of udder care according to claim 3, wherein such decolorizing composition also comprises an organic acid.

5. Method of post-milking udder care, comprising
    applying to the udder, after milding, an aqueous solution of an alkali metal hypochlorite and an alkali metal permanganate.

6. Method of udder care according to claim 5, wherein the hypochlorite concentration is about several volume percent.

7. Method of udder care according to claim 5, wherein the permanganate concentration is sufficient to color the udder.

8. Method of milking-related udder care, comprising applying to the udder, after milking, an aqueous solution of an alkali metal hypochlorite and an alkali metal permanganate, thereby disinfecting and coloring the udder; and applying before milking, to the udder so colored, an aqueous solution of hydrogen peroxide and acetic acid, thereby decolorizing and disinfecting the udder.

9. An udder-care kit comprising the respective solutions of claim 8.

10. Udder-care post-milkinq and pre-milking aqueous solutions, comprising several volume percent of alkali metal hypochlorite, plus a coloring amount of an alkali metal permanganate, in the post-milking solution; and several volume percent of hydrogen peroxide and a like amount of acetic acid in the pre-milking solution.

11. Apparatus for dispensing one or both of the solutions of claim 10, comprising a housing having at least one reservoir for such a solution, an inlet in the housing to receive such a solution thereinto, and a plurality of spray outlets oriented up from the housing.

12. Apparatus according to claim 11, including also control means for dispensing such a solution as required.

* * * * *

UNITED STATES PATENT AND TRADEMARK OFFICE
CERTIFICATE OF CORRECTION

PATENT NO. : 5,101,770

DATED : April 7, 1992

INVENTOR(S) : Dale V. Stevenson

It is certified that error appears in the above-identified patent and that said Letters Patent is hereby corrected as shown below:

COLUMN 4

Claim 2, lines 6, 7 and 8 should be deleted in their entirety.

Claim 3, line 3, change "organic acid" to --aqueous peroxide--.

Claim 5, line 2, change "milding" to --milking--.

Signed and Sealed this

Twentieth Day of October, 1992

Attest:

DOUGLAS B. COMER

*Attesting Officer*    *Acting Commissioner of Patents and Trademarks*